(12) United States Patent  
Weiman et al.

(10) Patent No.: US 10,548,744 B2  
(45) Date of Patent: Feb. 4, 2020

(54) INSERTION TOOL ASSEMBLY

(71) Applicant: GLOBUS MEDICAL, INC., Audubon, PA (US)

(72) Inventors: Mark Weiman, Coatesville, PA (US); Christopher Angelucci, Schwenksville, PA (US); Jason Gray, East Greenville, PA (US); Noah Hansell, King of Prussia, PA (US); Jeff Bennett, Pottstown, PA (US); Cameron Salzberger, Sinking Spring, PA (US)

(73) Assignee: Globus Medical, Inc., Audubon, PA (US)

( * ) Notice: Subject to any disclaimer, the term of this patent is extended or adjusted under 35 U.S.C. 154(b) by 271 days.

(21) Appl. No.: 15/340,014

(22) Filed: Nov. 1, 2016

(65) Prior Publication Data

US 2017/0042701 A1 Feb. 16, 2017

Related U.S. Application Data

(63) Continuation of application No. 14/867,392, filed on Sep. 28, 2015, now Pat. No. 9,510,957, which is a continuation of application No. 14/326,787, filed on Jul. 9, 2014, now Pat. No. 9,173,750, which is a continuation of application No. 12/764,682, filed on Apr. 21, 2010, now Pat. No. 8,808,304.

(51) Int. Cl.  
*A61F 2/46* (2006.01)  
*A61B 17/17* (2006.01)  
*A61F 2/44* (2006.01)  
*A61F 2/30* (2006.01)

(52) U.S. Cl.  
CPC ........ *A61F 2/4611* (2013.01); *A61B 17/1728* (2013.01); *A61B 17/1757* (2013.01); *A61F 2/4425* (2013.01); *A61F 2/4455* (2013.01); *A61F 2002/3082* (2013.01); *A61F 2002/30596* (2013.01); *A61F 2002/30884* (2013.01); *A61F 2002/4629* (2013.01)

(58) Field of Classification Search  
CPC .................................................... A61F 2/4611  
See application file for complete search history.

(56) References Cited

U.S. PATENT DOCUMENTS

| | | | |
|---|---|---|---|
| 5,667,513 A | 9/1997 | Torrie et al. | |
| 6,379,364 B1* | 4/2002 | Brace | A61B 17/1728 606/86 R |
| 7,094,242 B2* | 8/2006 | Ralph | A61B 17/1728 606/96 |
| 7,618,423 B1* | 11/2009 | Valentine | A61F 2/447 606/99 |
| 7,776,047 B2* | 8/2010 | Fanger | A61B 17/1757 606/96 |
| 8,328,851 B2 | 12/2012 | Curran et al. | |
| 8,840,668 B1* | 9/2014 | Donahoe | A61B 17/1604 623/17.16 |
| 2004/0204716 A1* | 10/2004 | Fanger | A61B 17/1728 606/96 |
| 2008/0133016 A1 | 6/2008 | Heinz | |

(Continued)

*Primary Examiner* — Nicholas W Woodall

(57) ABSTRACT

Insertion tool assemblies for positioning an implant at a target location in a patient. Insertion tool assemblies that comprise first and second jaw portions configured to engage an implant; a sleeve assembly coupled to the first and second jaw portions; and a handle coupled to the sleeve assembly.

20 Claims, 18 Drawing Sheets

(56) References Cited

U.S. PATENT DOCUMENTS

2008/0287957 A1  11/2008  Hester et al.
2009/0024132 A1* 1/2009  Blain ................. A61B 17/1728
                                                           606/96
2010/0100138 A1  4/2010  Reynolds et al.

* cited by examiner

INSERTION TOOL ASSEMBLY

CROSS REFERENCE TO RELATED APPLICATIONS

This patent application is a continuation of U.S. patent application Ser. No. 14/867,392, filed Sep. 28, 2015, which is a continuation of U.S. patent application Ser. No. 14/326,787, filed Jul. 9, 2014, now U.S. Pat. No. 9,173,750, which is a continuation of U.S. patent application Ser. No. 12/764,682, filed Apr. 21, 2010, now U.S. Pat. No. 8,808,304, which are incorporated by reference herein in their entireties for all purposes.

FIELD OF THE INVENTION

The present disclosure generally relates to treatment of spinal irregularities. In particular, in one or more embodiments, the present disclosure relates to insertion tool assemblies that can be used to position an implant at a target location in a patient.

BACKGROUND

Medical devices may be implanted in patients in a variety of different surgical procedures. In the treatment of spinal irregularities, for example, implants may be inserted within a space created by complete or partial removal of an intervertebral disc between adjacent vertebrae. One example of an implant that may be placed into the disc space of a patient's spine is a spacer that can maintain height of the spine and/or restore stability to the spine. Another example of an implant that can be placed into a patient's spine is an artificial disc that can replace the disc while maintaining vertebral height and also preserving mobility in the treated vertebral segment.

A spinal implant can be inserted into the patient using an anterior, lateral, or posterior approach. Combinations of these approaches (e.g., posterolateral) can also be used. In each of these approaches, the surgeon typically has little room to maneuver the implant to the desired location. In addition, while maneuvering the implant, the surgeon must use care to avoid organs, nerves, and other structures that could result in damage to the patient. Accordingly, insertion tool assemblies that can be used to position the implant in the patient should securely hold the implant without allowing articulation, e.g., flexion/extension, lateral bending or axial rotation. Further, the connection between the implant and the insertion tool assembly should be rigid enough for impaction when being used by the surgeon. In addition, the implant should be readily removed from the insertion tool assembly once it has been placed in the desired location within the patient.

Several different insertion tool assemblies have been used heretofore to position implants in a patient. For instance, one type of insertion tool assembly that has been used includes threaded connections for securing the implant to the holder. These threaded assemblies may also incorporate vertical grooves to further secure the implant. One drawback to threaded connections includes cross-threading and the resulting difficulties in placing the implant in the desired position. Another type of insertion tool assembly that has been used includes parallel vertical jaws for securing the implant to the assembly. These jaws may, for example, protrude into upper and lower keels on the implant. One drawback to the parallel jaws is that the jaws may have issues maintaining parallelism with regards to the upper and lower endplates in certain artificial discs.

Thus, there is a need for improved insertion tool assemblies that can securely hold the implant while placing the implant within the patient.

SUMMARY

An embodiment of the present invention provides an insertion tool assembly. The insertion tool may comprise a first and second jaw portions configured to engage an implant. The insertion tool assembly may comprise a sleeve assembly coupled to the first and second jaw portions. The insertion tool assembly may comprise a handle coupled to the sleeve assembly.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

These drawings illustrate certain aspects of the present invention and should not be used to limit or define the invention.

DETAILED DESCRIPTION OF THE ILLUSTRATED EMBODIMENTS

Embodiments of the present invention provide insertion tool assemblies that can be used to position an implant at a target location within a patient. Non-limiting examples of implants that may be used with the assemblies include spinal implants, such as spacers, artificial discs, and plates among others. Advantageously, the insertion tool assemblies should rigidly fix the implant to the assembly during insertion of the implant into the patient in accordance with embodiments of the present invention. Accordingly, the implant should generally remain fixed to embodiments of the assemblies during impaction and maneuvering when being used by the surgeon, for example. In certain embodiments, the insertion tool assemblies should be able to rigidly fix the implant to the assembly in embodiments where there is little surface area on the implant for gripping by the assembly. This may be particularly beneficial with certain implants, such as artificial discs.

Figure 1:
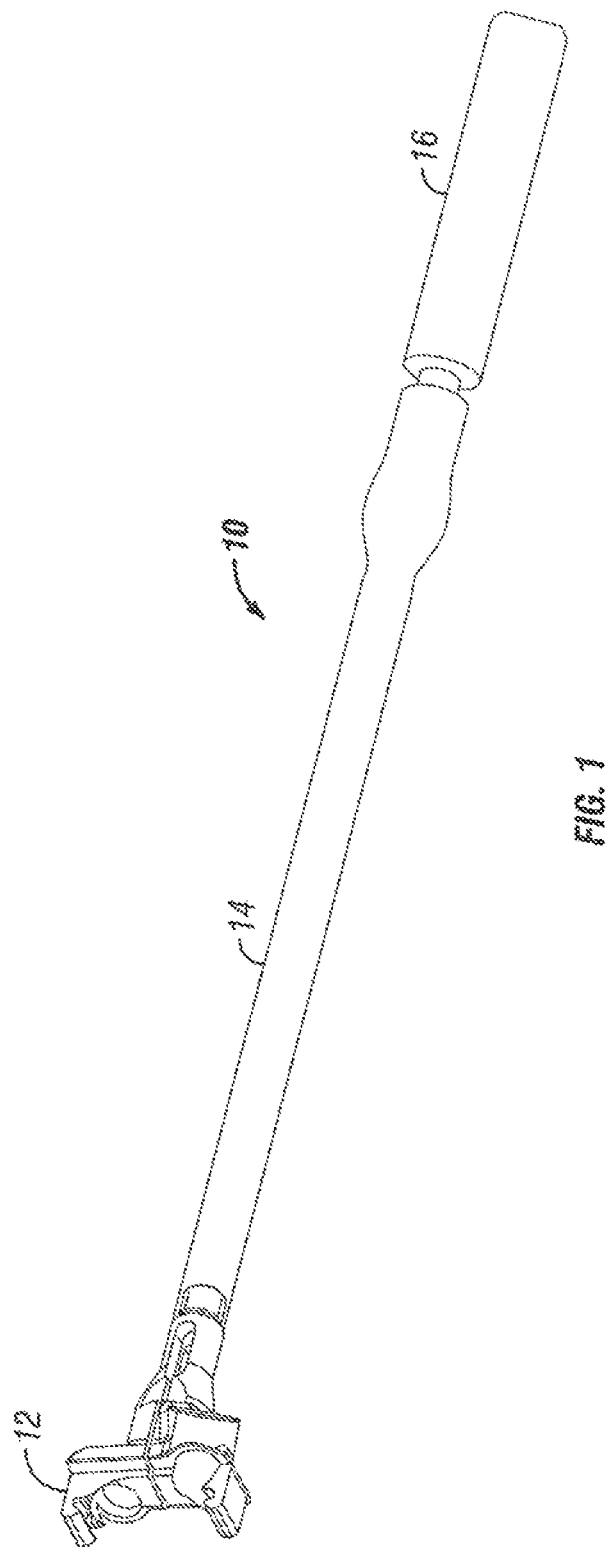
FIG. 1 illustrates an insertion tool assembly in accordance with one embodiment of the present invention.
Figure 2:
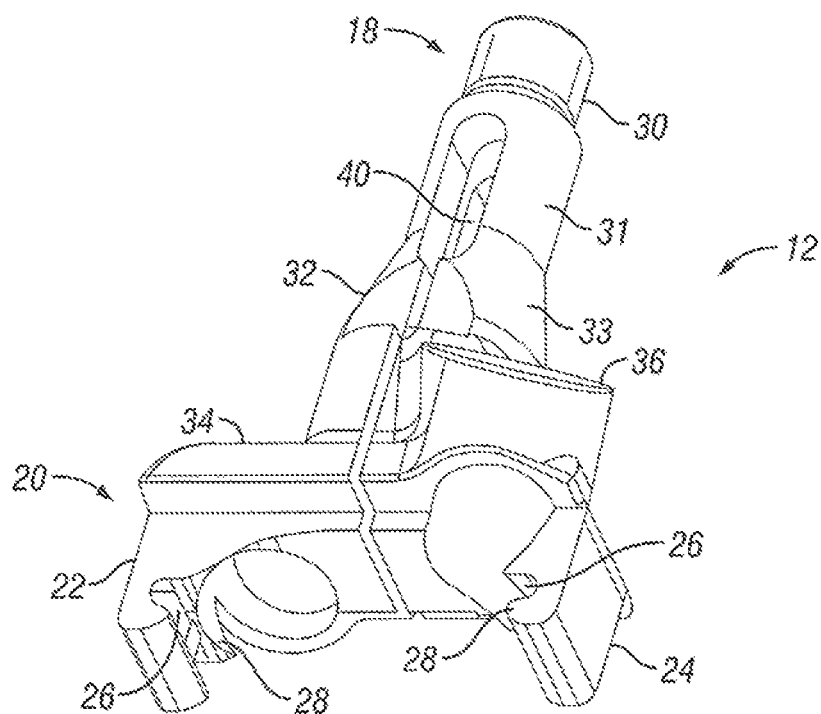
FIG. 2 is a perspective view of a gripping tip of an insertion tool assembly in accordance with one embodiment of the present invention.
Figure 3:
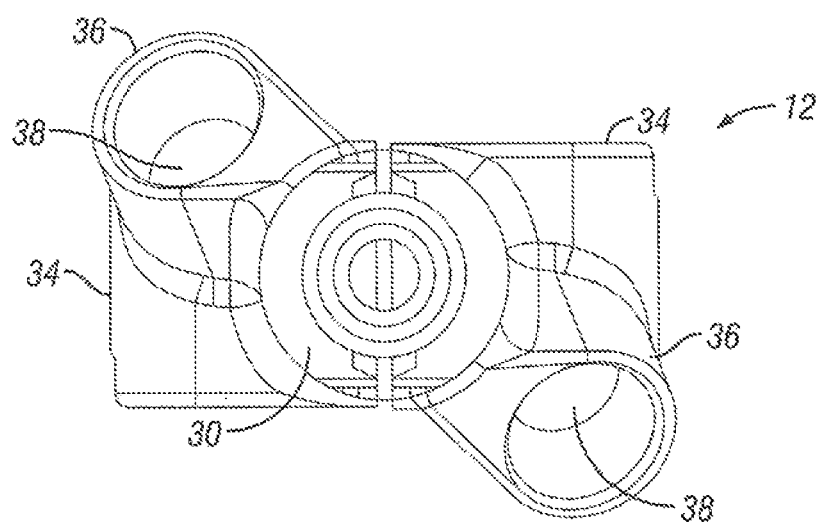
FIG. 3 is an end view of a gripping tip of an insertion tool assembly in accordance with one embodiment of the present invention.
Figure 4:
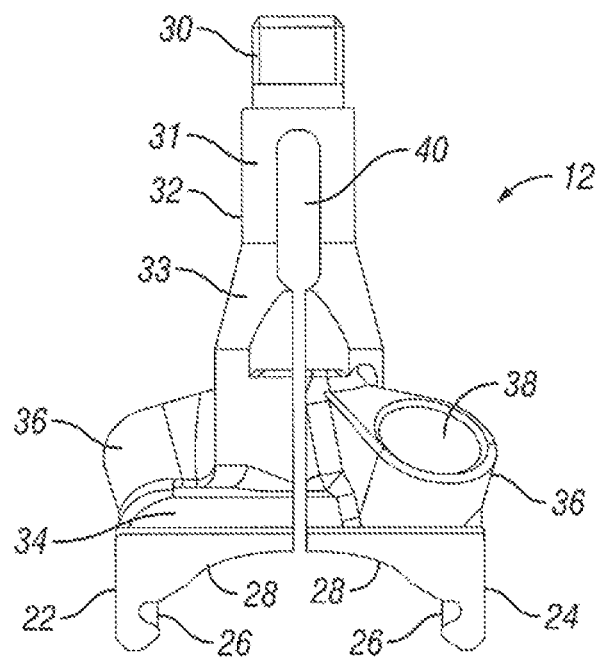
FIGS. 4 and 5 are side views of a gripping tip of an insertion tool assembly in accordance with one embodiment of the present invention.
Figure 5:
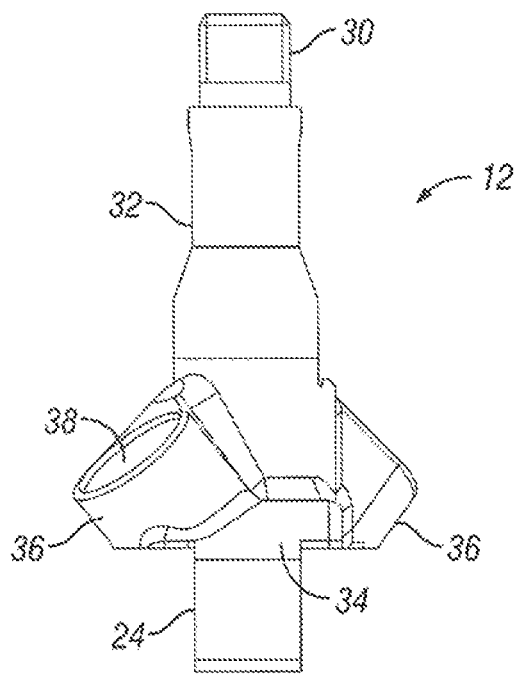

FIG. 1 illustrates an insertion tool assembly 10 in accordance with one embodiment of the present invention. As illustrated, the insertion tool assembly 10 may comprise a gripping tip 12, a sleeve assembly 14, and a handle assembly 16. The gripping tip 12 should generally be configured to engage an implant and fixedly couple the implant to the insertion tool assembly 10. When a physician has maneuvered the implant to a desired location with the patient, the gripping tip 12 should be configured to release the implant. The gripping tip 12 is generally coupled to a sleeve assembly 14 that is disposed between the gripping tip 12 and the handle assembly 16 in the illustrated embodiment. In accordance with the present embodiments, the sleeve assembly 14 may comprise one or more tubes or sleeves. As illustrated, the handle assembly 16 may be coupled to the sleeve assembly 14. In an embodiment, a physician may engage the handle assembly 16 to maneuver the implant to a target location with the patient.

FIGS. 2-5 illustrate a gripping tip 12 for an insertion tool assembly 10 (see, e.g., FIG. 1) having a proximal end 18 and a distal end 20 in accordance with one embodiment of the present invention. In the illustrated embodiment, the distal end 20 of the gripping tip 12 includes a first jaw portion 22 and second jaw portion 24. The first and second jaw portions 22, 24 may be configured to close to fixedly secure the implant to the insertion tool assembly 10. The gripping tip 12 may further include a keyed protrusion 26. As illustrated, each of the first and second jaw portions 22, 24 may include a keyed protrusion 26 on an interior surface 28 of the jaw portions 22, 24 that engage the implant. In certain embodiments, the keyed protrusion 26 may be configured to engage with a corresponding guide or recess on the implant so that the implant can be fixed to the insertion tool assembly 10 as desired. In an embodiment, the guide/recess on the implant should be capable of engaging with the keyed protrusion 26 at only one angle and orientation. The proximal end 18 of the gripping tip 12 may include a threaded portion 30 for coupling the gripping tip 12 to the sleeve assembly 14. The gripping tip 12 may include a body portion 32 disposed between the first and second jaw portions 22, 24 and the threaded portion 30. As illustrated, the body portion 32 may be generally cylindrical in shape and also may include an exterior surface 31 having a tapered portion 33.

In accordance with embodiments of the present invention, the gripping tip 12 may further include a flanged portion 34. As illustrated, each of the first and second jaw portions 22, 24 may extend outwardly from the outer edges of the flanged portion 34 in the direction of the longitudinal axis of the gripping tip 12. The flanged portion 34 may include at least one (e.g., two) drill guide 36, which may be attachments to, or openings in, the flanged portion 34. The drill guide 36 should generally be configured to facilitate fixed angle drilling and/or screw insertion, for example. As illustrated, each drill guide 36 may include a hole 38 through which devices (e.g., drills, screws, etc.) can be inserted. In an embodiment, the holes 38 in the drill guides 36 are angled inwardly (e.g., toward one another). As illustrated, one of the holes 38 may be angled upwardly with the other hole 38 angled downwardly.

As illustrated by FIGS. 2-5, the gripping tip 12 may have a slot 40 that extends from the proximal end 18 to the distal end 20 to allow flexing of the tip 12. In the illustrated embodiment, the slot 40 extends from the flanged portion 34 to the body portion 32. In an embodiment, the slot 40 may be open on the distal end 20 of the gripping tip 12. In accordance with embodiments of the present invention, the slot 40 should generally allow flexing of the gripping tip 12 so that the first and second jaw portions 22, 24 can clamp down onto an implant or release the implant. As illustrated, the slot may narrow in the tapered portion 33 of the body portion 32.

Figure 6:
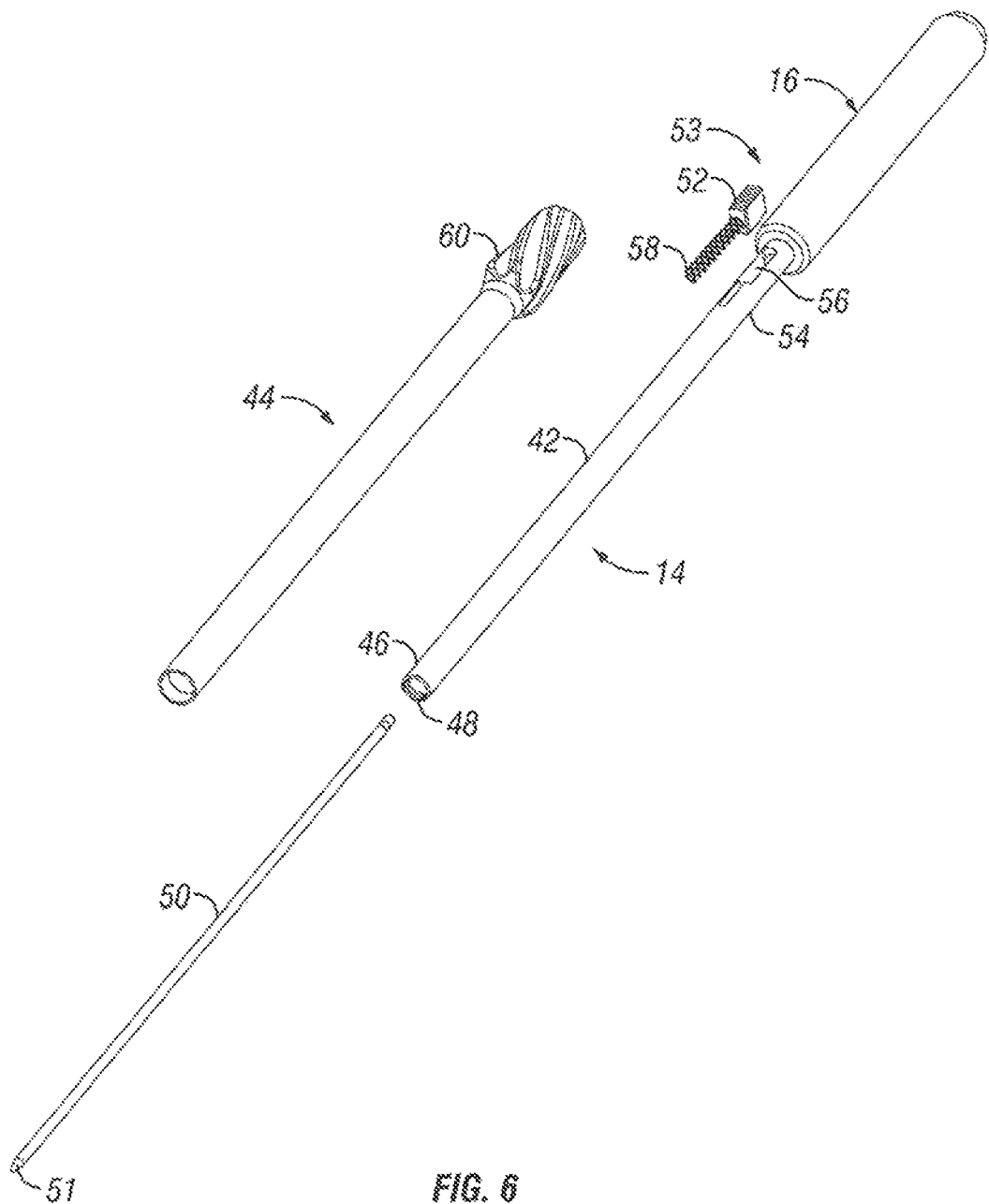
FIGS. 6 and 7 are exploded views of a sleeve assembly and handle assembly for an insertion tool assembly in accordance with one embodiment of the present invention.
Figure 7:
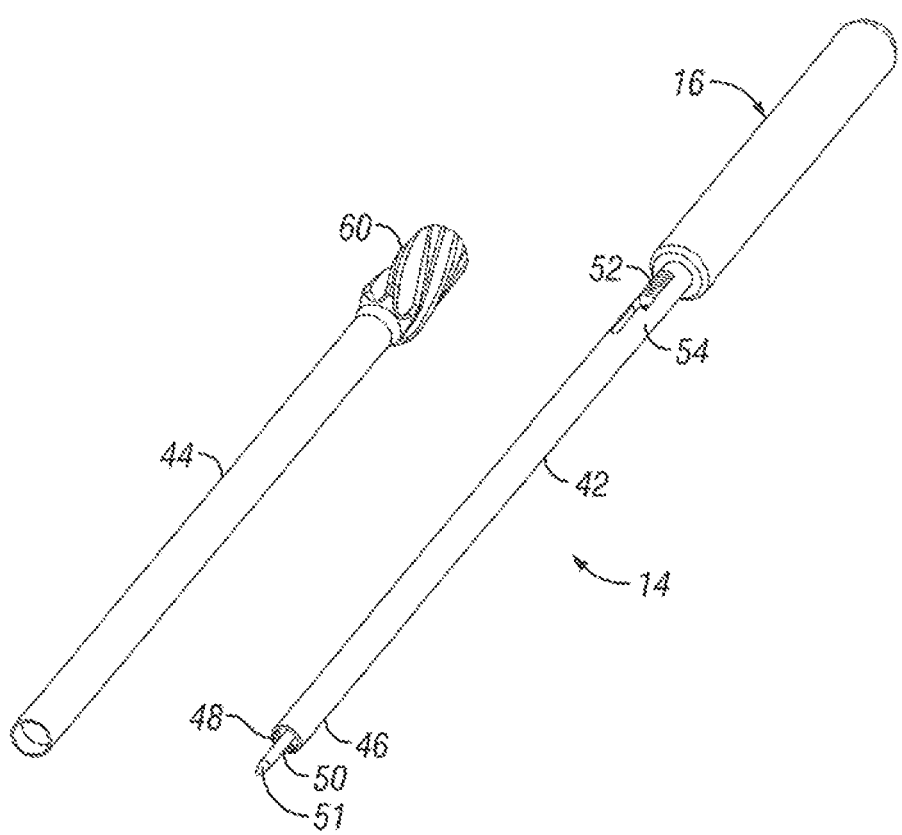

FIGS. 6 and 7 illustrate exploded views of the sleeve assembly 14 and handle assembly 16 for an insertion tool assembly 10 (see, e.g., FIG. 1) in accordance with one embodiment of the present invention. FIGS. 8-13 illustrate additional views of the sleeve assembly and handle assembly 16 in accordance with embodiments of the present invention. As illustrated, the sleeve assembly 14 includes an inner sleeve 42 and an outer sleeve 44 that is disposed over the inner sleeve 42 when assembled with the inner sleeve 42 generally configured for attachment to the gripping tip 12. In an embodiment, the distal end 46 of the inner sleeve 42 contains threads 48 for forming a threaded connection with the threaded portion 30 of the gripping tip 12. As illustrated, the outer sleeve 44 may be configured to move along the outer surface of the inner sleeve 42. As will be discussed in more detail below with respect to FIGS. 8-11, the outer sleeve 44 may move down the inner sleeve 42 to lock the gripping tip 12 onto the implant in accordance with embodiments of the present invention.

Figure 10:
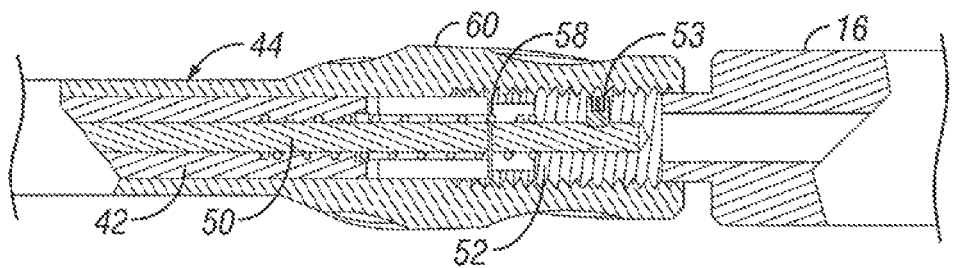
FIG. 10 is a partial cross-sectional view of the proximal end of an insertion tool assembly in the locked position in accordance with one embodiment of the present invention.
Figure 11:
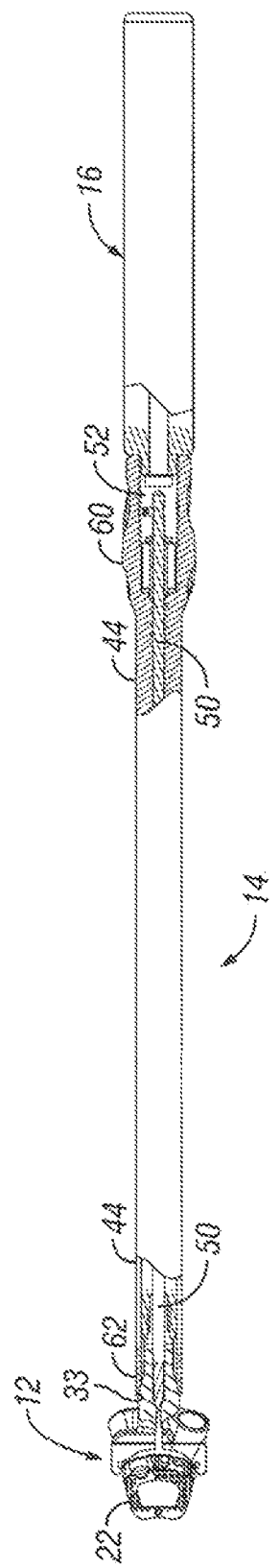
FIG. 11 is a partial cross-sectional view of an insertion tool assembly in the unlocked position in accordance with one embodiment of the present invention.
Figure 12:
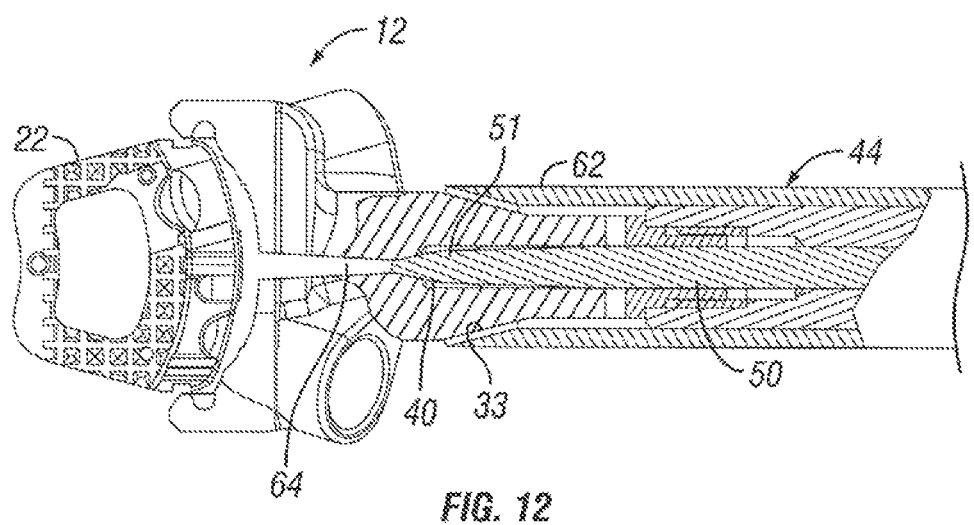
FIG. 12 is a partial cross-sectional view of the distal end of an insertion tool assembly in the unlocked position in accordance with one embodiment of the present invention.
Figure 13:
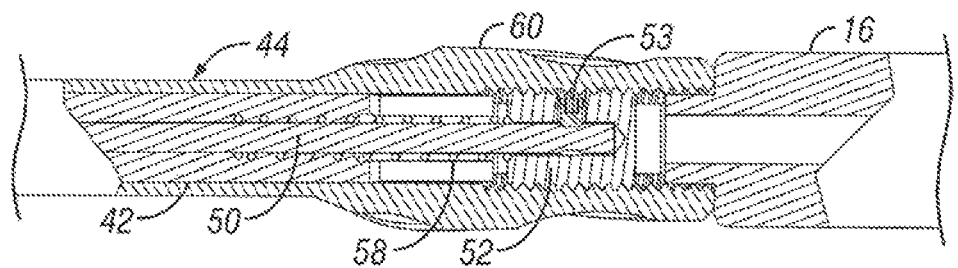
FIG. 13 is a partial cross-sectional view of the proximal end of an insertion tool assembly in the unlocked position in accordance with one embodiment of the present invention.

In the illustrated embodiment, the sleeve assembly 14 further includes a plunger 50 that is disposed inside the inner sleeve 42. The plunger 50 may include, for example, a tip 51 that extends through the distal end 46 of the inner sleeve 42. As illustrated, the plunger 50 may be coupled to a threaded nut 52. A set screw 53, for example, may be used to fix the plunger 50 to the threaded nut 52. The threaded nut 52 may be disposed in the proximal end 54 of the inner sleeve 42. In the illustrated embodiment, the inner sleeve 42 includes at least one (e.g., two) slot 56 in its proximal end 54 through which the exterior threads of the threaded nut 52 extend. The slot 56 allows for translation of the threaded nut 52 within the inner sleeve 42. As illustrated by FIG. 10, the proximal end 60 of outer sleeve 44 can be threaded onto the threads of the threaded nut 52. The sleeve assembly 14 may further include a spring 58 in the inner sleeve 42 with the spring 58 engaging the threaded nut 52, in accordance with an embodiment. In an embodiment, the spring 58 provides force to maintain engagement between the threaded nut 52 and the handle assembly 16. In other words, the spring 58 prevents the threaded nut 52 from freely sliding within the inner sleeve 42 and pushes the nut 52 toward the proximal end of the slot 56 in the inner sleeve 42.

Figure 8:
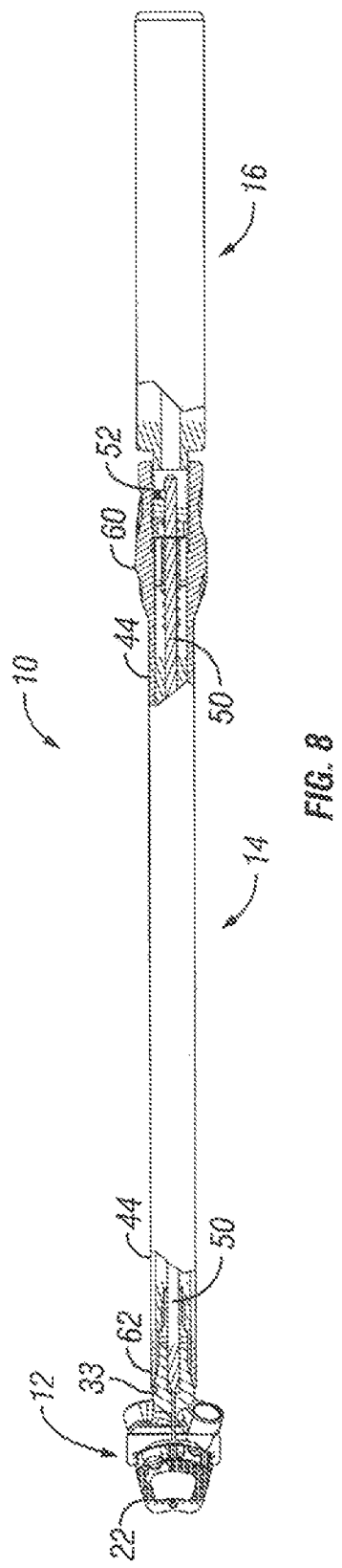
FIG. 8 is a partial cross-sectional view of an insertion tool assembly in the locked position in accordance with one embodiment of the present invention.
Figure 9:
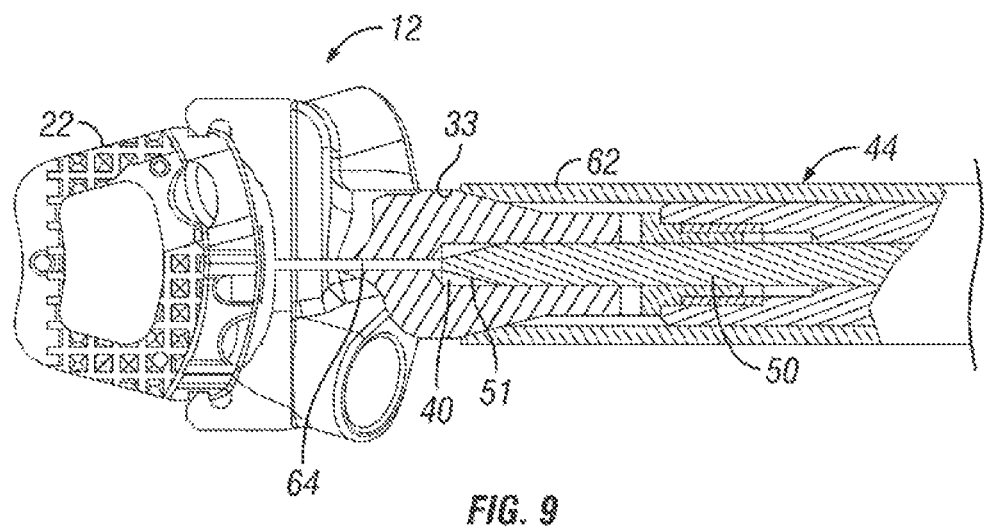
FIG. 9 is a partial cross-sectional view of the distal end of an insertion tool assembly in the locked position in accordance with one embodiment of the present invention.

FIGS. 8-10 illustrate the insertion tool assembly 10 (see, e.g., FIG. 1) with the gripping tip 12 in a locked position in accordance with one embodiment of the present invention. The insertion tool assembly 10 may be placed in the locked position, for example, to secure the gripping tip 12 to an implant. To place the insertion tool assembly 10 in a locked position in accordance with one embodiment, the outer sleeve 44 can be forced down the inner sleeve 42 and onto the gripping tip 12. As the distal end 62 of the outer sleeve engages the beveled surface 33 of the gripping tip 12, the gripping tip 12 should flex closing the first and second jaw portions 22, 24 onto the implant. In this manner, the implant may be rigidly fixed to the insertion tool assembly 10 in accordance with one embodiment of the present invention. The surgeon may then maneuver the implant to the desired position in the patient, for example.

In the embodiment illustrated by FIGS. 8-10, the plunger 50 is disposed in the slot 40 of the gripping tip 12 when the insertion tool assembly 10 is in the locked portion. As illustrated, the slot 40 includes a narrow portion 64 having a diameter less than the diameter of the plunger 50. In an embodiment, the narrow portion 64 is generally in the beveled portion 33 of the gripping tip 12.

FIGS. 11-14 illustrate the insertion tool assembly 10 (see e.g., FIG. 1) with the gripping tip 12 in an unlocked position in accordance with one embodiment of the present invention. The insertion tool assembly 10 may be placed in the unlocked position, for example, to release the implant from the gripping tip 12. The implant may be released from the insertion tool assembly 10, for example, after it has been maneuvered to the desired position within the patient. To place the insertion tool assembly 10 in an unlocked position in accordance with one embodiment, the tip 51 of the plunger 50 can be forced into the narrow portion 64 of the slot 40. This should cause the gripping tip 12 to flex outwardly forcing open the first and second jaw portions 22, 24 releasing the implant. In an embodiment, the plunger 50 may be forced further into the slot 40 by tightening the outer sleeve 44 against the handle assembly 16. As illustrated, tightening the outer sleeve 44 may engage the threaded nut 52 such that tightening the outer sleeve 44 should force the threaded nut 52 and, thus, the plunger 50, further down the inner sleeve 42. It should be understood that other suitable techniques for forcing the plunger 50 further into the slot 40 may be used in accordance with embodiments of the present invention.

Figure 14:
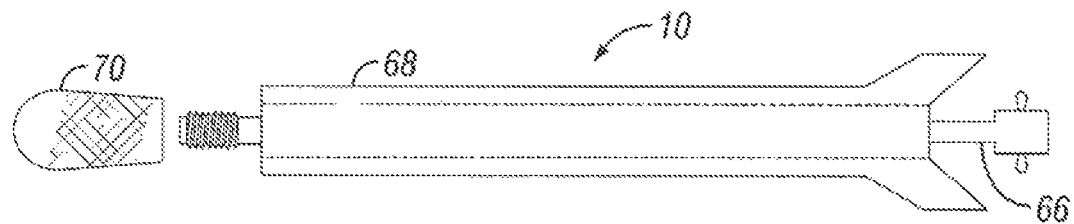
FIG. 14 is a side view of an insertion tool assembly in accordance with one embodiment of the present invention.
Figure 15:
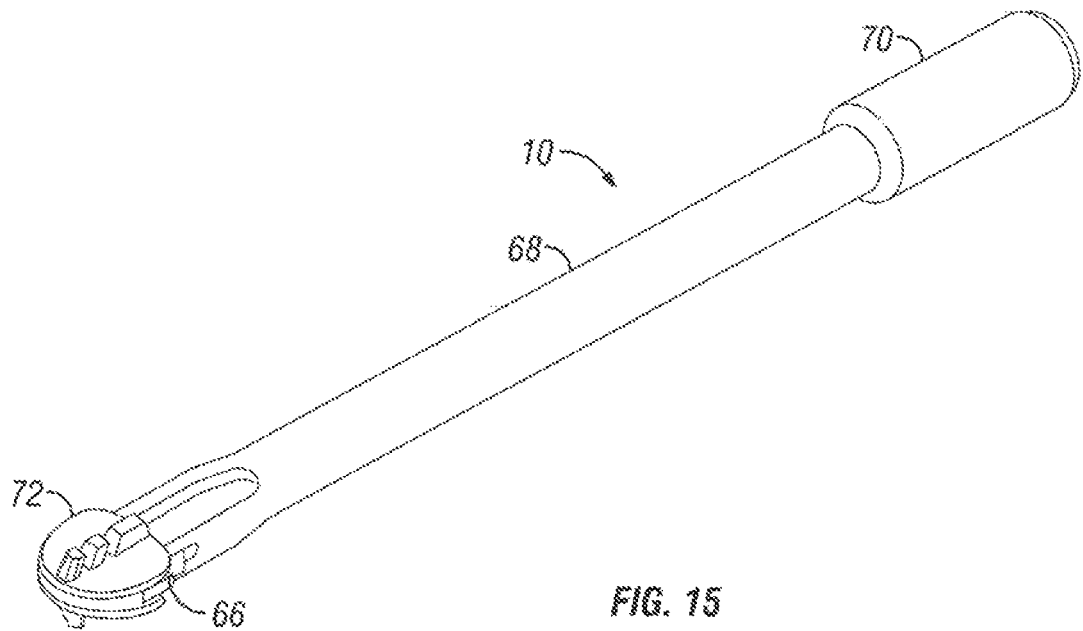
FIG. 15 is a perspective view an insertion tool assembly holding an implant in accordance with one embodiment of the present invention.

FIGS. 14 and 15 illustrate an insertion tool assembly 10 in accordance with another embodiment of the present invention. As illustrated, the insertion tool assembly 10 may comprise a retractable insertion device 66, a sleeve 68 disposed over the retractable insertion device 66, and a handle 70. As illustrated by FIG. 15, the retractable insertion device 66 may hold an implant 72 while the implant 72 is gripped between ends of the sleeve 68. Operation of the insertion tool assembly 10 for holding the implant 72 will be described in more detail with reference to the following figures.

Figure 16:
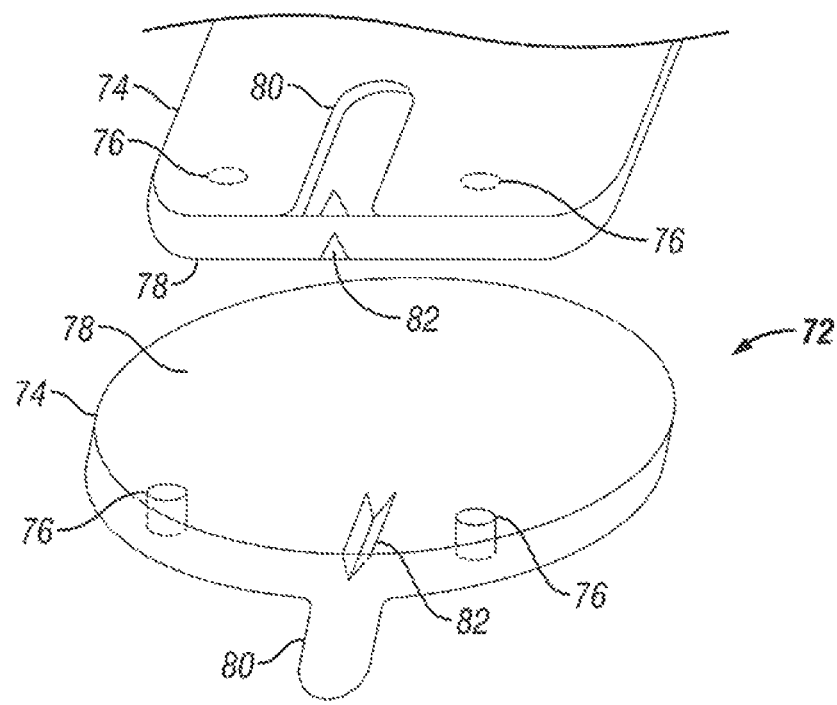
FIGS. 16 and 17 illustrate views of an implant for use with an insertion tool assembly in accordance with one embodiment of the present invention.
Figure 17:
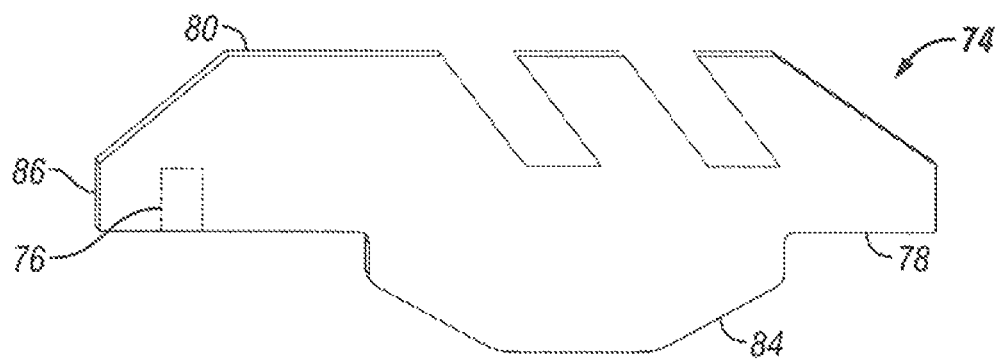

As previously mentioned, insertion tool assemblies of the present invention may be used with a wide variety of implants, such as spacers and artificial discs. FIGS. 16 and 17 illustrate an implant 72 (e.g., an artificial disc) that can be used with insertion tool assembly 10. In an embodiment, the implant 72 may be used, for example, with the insertion tool assembly 10 illustrated by FIGS. 14 and 15. As illustrated, the implant 72 may comprise endplates 74. Each of the endplates 74 may comprise one or more (e.g., two) holes 76 in the inner face 78. In the illustrated embodiment, the holes 76 are blind holes. As illustrated, each of the endplates may further comprise at least one (e.g., two) keel 80. In an embodiment, the inner face 78 of each of the endplate 74 contains an alignment groove 82. In addition, the inner face 78 of each endplate may also contain protruding portion 84, which as illustrated by FIG. 17 may be rounded. In an embodiment, the holes 76 may be disposed in the inner face 78 between the protruding portion 84 and the anterior end 86.

Figure 18:
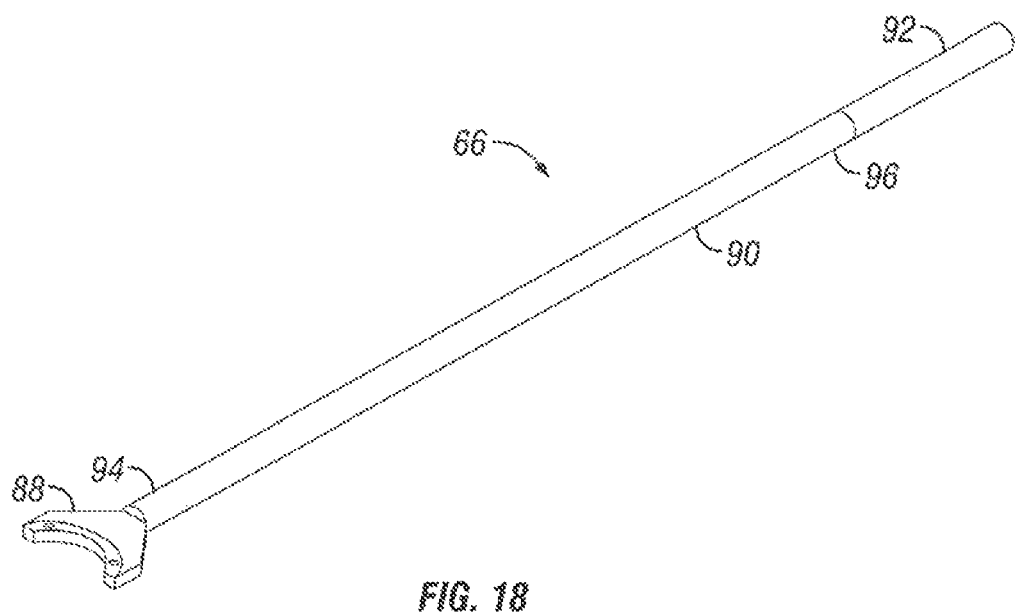
FIG. 18 is a perspective view of an insertion device for an insertion tool assembly in accordance with one embodiment of the present invention.
Figure 19:
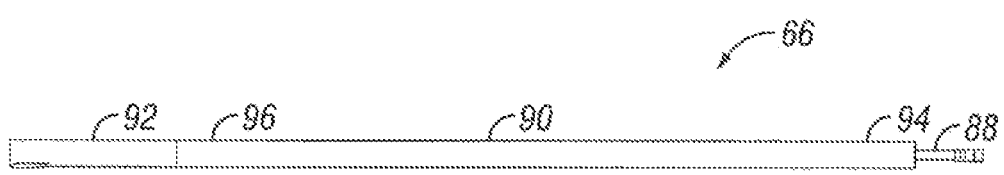
FIG. 19 is a side view of an insertion device for an insertion tool assembly in accordance with one embodiment of the present invention.

FIGS. 18 and 19 illustrate a retractable insertion device 66 for an insertion tool assembly 10 (see, e.g., FIGS. 15 and 16) in more detail in accordance with one embodiment of the present invention. As illustrated, the retractable insertion device 66 may comprise a holding device 88, a rod portion 90, and a threaded portion 92. The holding device 88 may be disposed on the distal end 94 of the rod portion 90. As will be discussed in more detail below, the holding device 88 may be configured to interlock with an implant, such as implant 72 on FIGS. 16 and 17. The threaded portion 92 may be disposed on the proximal end 96 of the rod portion 90. In an embodiment, the threaded portion 92 may be configured to threadedly connect with the handle 70 (see, e.g., FIG. 14).

Figure 20:
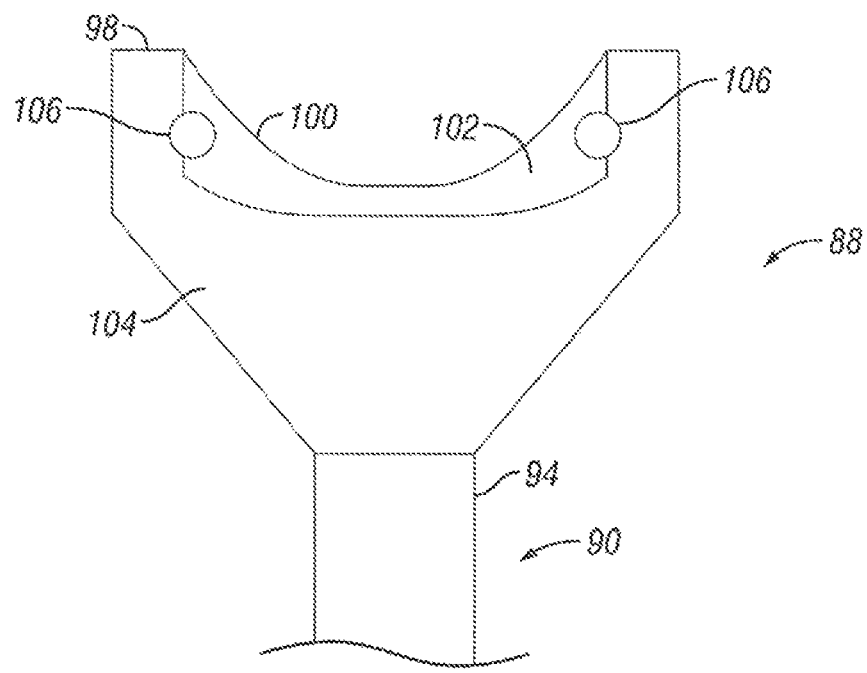
FIG. 20 is a top view of a holding mechanism for an insertion tool assembly in accordance with one embodiment of the present invention.

FIG. 20 illustrates a holding device 88 for an insertion device 66 (see, e.g., FIGS. 18 and 19) in accordance with one embodiment of the present invention. The insertion device 66 may be coupled to the distal end 94 of the rod portion 90. In the illustrated embodiment, the holding device 88 may be generally paddle shaped. As illustrated, the outer edge 98 of the holding device 88 may have a concave portion 100. However, it should be understood that the alternate embodiments may include an outer edge that is straight or convex, for example. In an embodiment, the concave portion 100 of the outer edge 98 has a beveled surface 102. The upper face 104 of the holding device 88 may comprise one or more (e.g., two) holes 106 for receiving pins (e.g., pins 108 on FIG. 21). In an embodiment, the holes 106 are blind holds. In certain embodiments, the pins may be configured to engage with corresponding holes in the implant (e.g., holes 76 on FIGS. 16 and 17). While not illustrated, the holding device 88 may comprise a lower face that is similar to the upper face 104 in that the lower face may include one or more holes for receiving pins that interlock the holding device 88 with an implant in accordance with one embodiment of the present invention. For example, the pins in the upper face 104 may be configured to engage with holes 76 in the inner face 78 of an endplate 74 (see, e.g., FIG. 14) while the lower face may interlock with holes 76 in the inner face 78 of the opposing endplate 74 (see, e.g., FIG. 14), securing the implant 72 to the holding device 88. In an embodiment, the pins may be configured to retract so that the implant can be released as desired.

Figure 21:
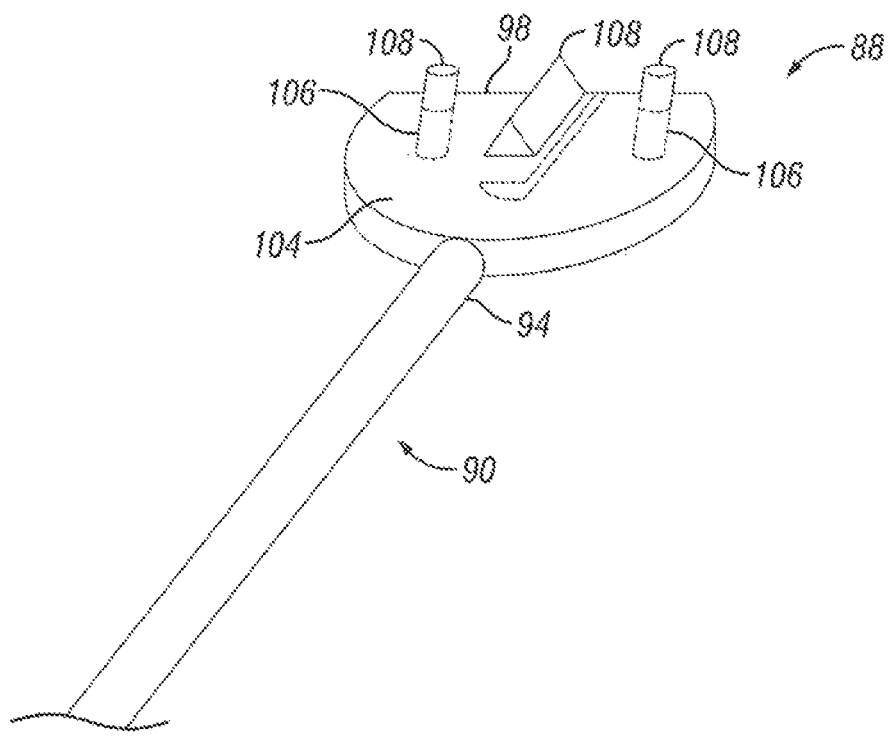
FIG. 21 illustrates another view of a holding mechanism for an insertion tool assembly in accordance with one embodiment of the present invention.

FIG. 21 illustrates another embodiment of a holding device 88 for an insertion device 66 (see, e.g., FIGS. 18 and 19). The holding device 88 is similar to the device illustrated on FIG. 19. For example, the holding device 88 is generally paddle shaped and comprises pins 108 in holes 106 for interlocking the insertion device 66 in accordance with embodiments of the present invention. However, rather than having an outer edge 98 with a concave portion 100 as illustrated on FIG. 19, the embodiment of FIG. 20 illustrates an outer edge 98 that is generally straight in shape. In addition, the holding device 88 of this embodiment comprises a wedge 110 that protrudes from the upper face 104 of the holding device 88. In certain embodiments, the wedge 110 may be configured to engage with a corresponding opening in the implant 72 (e.g., alignment groove 82 on FIG. 14) so that the holding device 88 can be fixed to the implant 72 as desired. In an embodiment, the wedge 110 of the holding device 88 is capable of engaging with the alignment groove 82 at only one angle and orientation.

Figure 22:
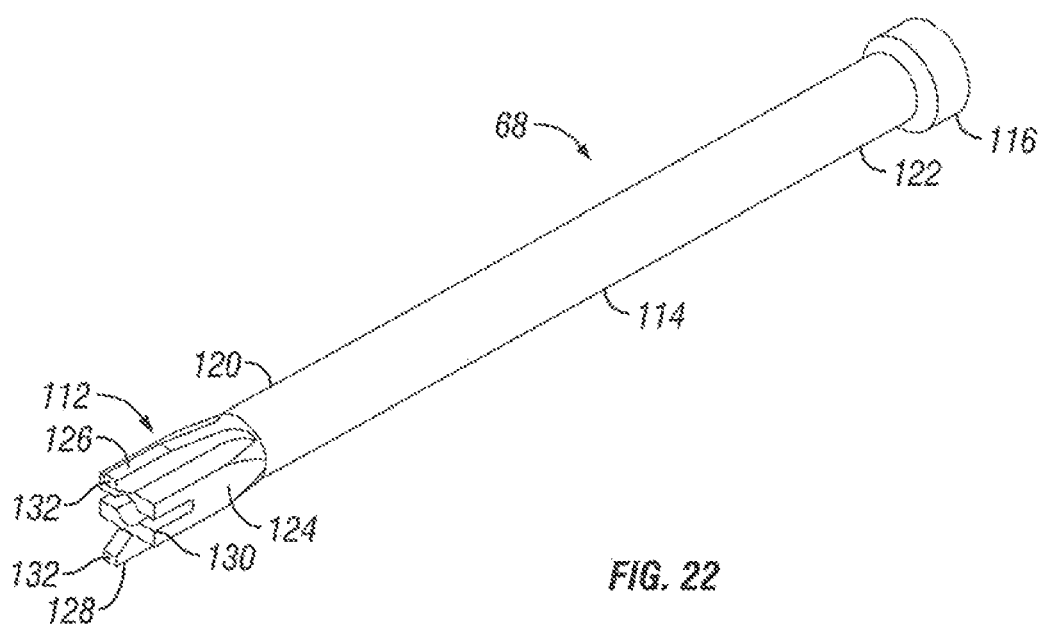
FIG. 22 is a perspective view of a sleeve for an insertion tool assembly in accordance with one embodiment of the present invention.
Figure 23:
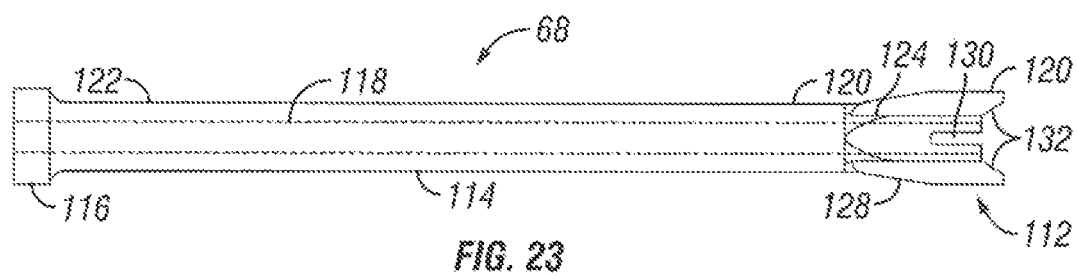
FIG. 23 is a side view of a sleeve for an insertion tool assembly in accordance with one embodiment of the present invention.
Figure 24:
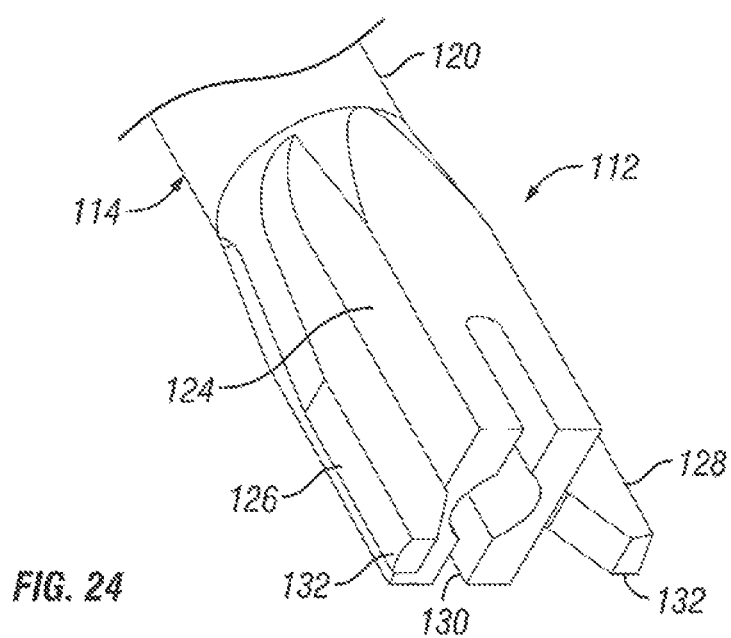
FIG. 24 is a perspective of implant holding jaws for an insertion tool assembly in accordance with one embodiment of the present invention.

FIGS. 22-24 illustrate a sleeve 68 having implant holding jaws 112 in accordance with one embodiment of the present invention. As illustrated, the sleeve 68 comprises implant holding jaws 112, sleeve portion 114, and a flanged end 116. In the illustrated embodiment, the sleeve 68 comprises a throughbore extending 118 longitudinally through the sleeve 68, for example. The implant holding jaws 112 may be disposed on the distal end 118 of the sleeve portion 114. As will be discussed in more detail below, the implant holding jaws 112 may be configured to engage the implant 72 (see, e.g., FIG. 15). The flanged end 116 may be disposed on the proximal end 122 of the sleeve 68.

As illustrated by FIGS. 22-24, the implant holding jaws 112 generally may comprise a body portion 124 having a first jaw portion 126 and a second jaw portion 128. In the illustrated embodiment, the throughbore 118 in the sleeve 68 enlarges to form a slot 130 in the body portion 124 of the implant holding jaws 112. In other words, the entrance to the throughbore 68 is a slot 130 in the body portion 124 of the implant holding jaws 112 in accordance with certain embodiments. Embodiments of the implant holding jaws 112 may comprise a first jaw portion 126 and second jaw portion 128 configured to engage an implant. For example, the first and second jaw portions 126, 128 may engage, for example, an upper face of an implant 72 as illustrated by FIG. 15. For example, the first and second jaw portions 126, 128 may be configured to engage an angled portion of the keel extending from the upper face of the implant 72. As illustrated, at least a portion the first and second jaw portions 126, 128 may be protrusions or raised surfaces on opposite sides of the body portion 124 with the jaw tips 130 extending beyond the edge of the body portion 124. In an embodiment, the implant 72 (see, e.g., FIG. 15) is held between the jaw tips 130. In the illustrated embodiment, the jaw tips 130 form a flared opening for receiving the implant 72.

An example method for holding the implant 72 with the insertion tool assembly 10 will be described in more detail with respect to FIGS. 14-24. An embodiment for holding the implant 72 includes coupling the implant 72 to the retractable insertion device 66. Coupling the implant 72 to the retractable insertion device 66 may include disposing one or more pins 108 on an upper face 104 of the retractable insertion device 66 into one or more corresponding holes 76 in an endplate 74 of the implant 72. Coupling the implant 72 further may include disposing one or more pins 108 on a lower face of the retractable insertion device 66 into one or more corresponding holes 76 in another endplate 74 of the implant 72. With the implant 72 coupled to the retractable insertion device 66, the insertion device 66 may be retracted into the sleeve 68. Retracting the insertion device 66 into the sleeve 68 may include rotation of the handle 70. As illustrated by FIG. 18, a portion of the retractable insertion device 66 may retract into the slot 130 in the body portion 124 of the implant holding jaws 112. As the retractable insertion device 66 retracts into the sleeve 68, the implant holding jaws 112 of the sleeve 68 should engage the implant 72. In an embodiment, the implant holding jaws 112 should force together the endplates 74 of the implant 72. In this manner, the implant 72 may be rigidly fixed to the insertion tool assembly 10 in accordance with one embodiment of the present invention. The surgeon may then maneuver the implant 72 to the desired position in the patient, for example.

As previously described with respect to FIGS. 1-13, embodiments of the insertion tool assemblies of the present invention may comprise a gripping tip 12. FIGS. 25-29 illustrate alternative embodiments of a gripping tip 12 that may be used to secure an implant to the insertion tool assembly 10. In an embodiment, the gripping tip 12 illustrated by FIGS. 25-29 may be used with a sleeve assembly 14 and handle assembly 16 as illustrated by FIGS. 1-13. It should be understood, however, that the gripping tip 12 illustrated in these figures may also be used in conjunction with other tube assemblies and handle assemblies in accordance with embodiments of the present invention.

Figure 30:
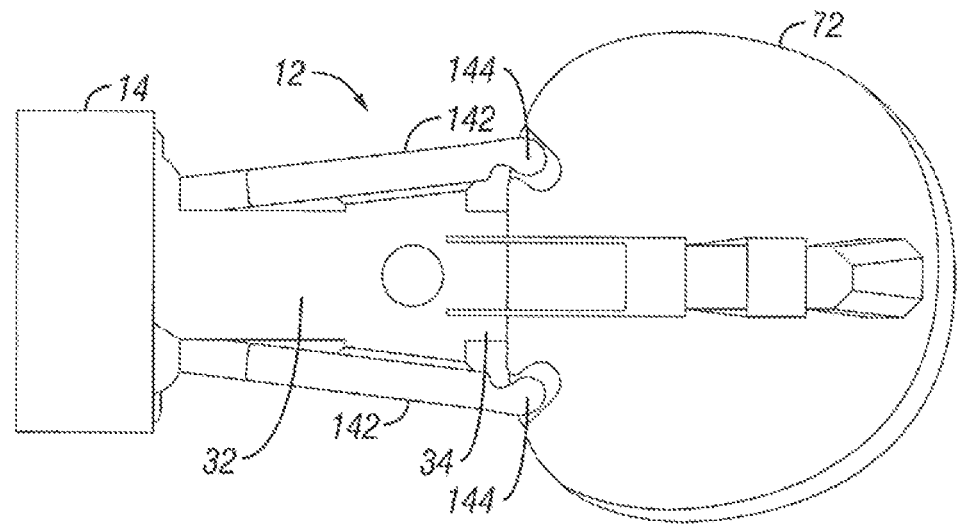
FIG. 30 is a top view of a gripping tip of an insertion tool assembly in a locked position and holding an implant in accordance with one embodiment of the present invention.
Figure 31:
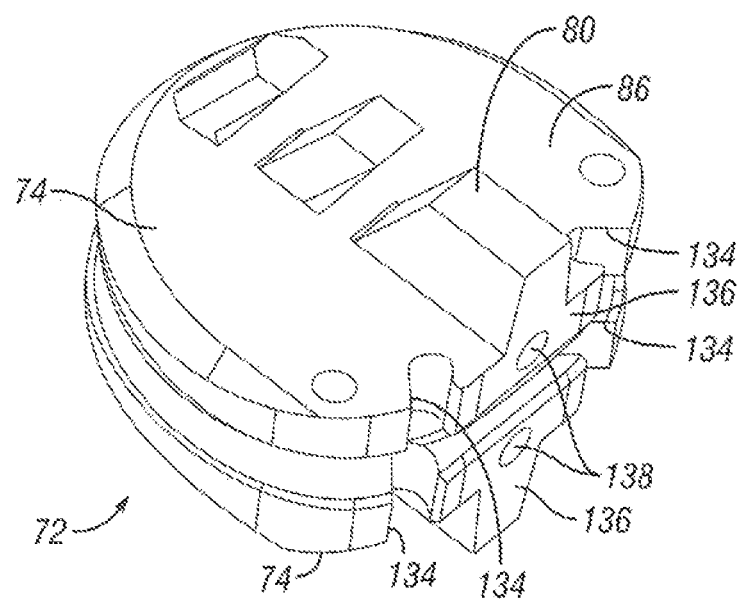
FIG. 31 is a perspective view of an implant for use with an insertion tool assembly in accordance with one embodiment of the present invention.

FIG. 31 illustrates an implant 72 (e.g., an artificial disc) that can be used with insertion tool assembly 10. In an embodiment, the implant 72 may be used, for example, with the insertion tool assembly 10 illustrated by FIGS. 25-30. As illustrated, the implant 72 may comprise endplates 74. Each of the endplates 74 may comprise one or more (e.g., two) lateral slots 134. In the illustrated embodiment, the lateral slots 134 are located on the anterior end 86 of the implant 72. As illustrated, the lateral slots 134 may be symmetrical along the central axis of the implant 72. In an alternate embodiment, one or more (e.g., two) lateral slots 134 may be located in the posterior end of the implant 72 in addition to, or instead of, the lateral slots 134 in the anterior end 86. In addition, the anterior face 136 of each of the endplates 74 may contain one or more (e.g., two) openings 138. Non-limiting examples of the openings 138 include slots, round holes, and square holes. In an alternate embodiment, one or more (e.g., two) openings may be located in the posterior end of the implant 72 in addition to, or instead of, the openings 138 in the anterior end 86. As illustrated, each of the endplates may further comprise at least one (e.g., two) keel 80.

Figure 25:
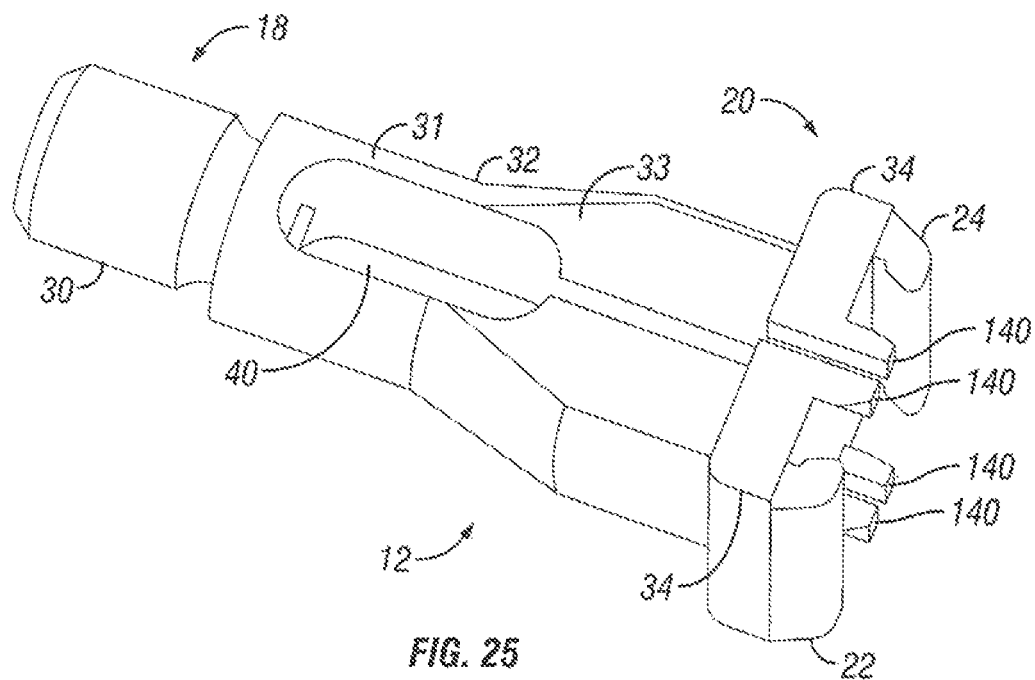
FIG. 25 is a perspective view of a gripping tip of an insertion tool assembly in accordance with one embodiment of the present invention.

FIG. 25 illustrates a gripping tip 12 that may be used to secure an implant to the insertion tool assembly 10 in accordance with one embodiment of the present invention. As illustrated, the gripping tip 12 has a proximal end 18 and a distal end 20 in accordance with one embodiment of the present invention. In the illustrated embodiment, the gripping tip 12 includes a threaded portion 30, a body portion 32, and a flanged portion 34. The threaded portion 30 may be disposed, for example, on the proximal end 18 of the gripping tip 12 for coupling the gripping tip 12 to the sleeve assembly 14. The body portion 32 may be disposed, for example, between the threaded portion 30 and the flanged portion 34. As illustrated, the body portion 32 may be generally cylindrical in shape and also may include an exterior surface 31 having a beveled portion 33.

In the illustrated embodiment, the distal end 20 of the gripping tip 12 may include a first jaw portion 22 and a second jaw portion 24. The first and second jaw portions 22, 24 may be configured to close to fixedly secure the implant to the insertion tool assembly 10. In an embodiment, the first and second jaw portions 22, 24 may be configured to engage with the lateral slots 134 in the endplates 74 of the implant (see, e.g., FIG. 31). As illustrated, the first and second jaw portions 22, 24 may be generally curved or rounded shape. In an embodiment, the first and second jaw portions 22, 24 extend outwardly and longitudinally from the outer edges of the flanged portion 34. One or more (e.g., two, four, etc.) projections 140 may also extend outwardly and longitudinally from the flanged portion 34. As illustrated, the projections 140 may extend outwardly from the flanged portion 34 on the edge of slot 40. The projections 140 may be, for example, round or elliptical pins. The projections 140 may be generally configured to engage with corresponding openings 138 in the implant 72 (see, e.g., the implant 72 illustrated on FIG. 31). In an embodiment, the projections 140 should engage the implant 72 to, for example, stabilize the implant 72 from twisting or being able to articulate.

In the embodiment illustrated by FIG. 25, the gripping tip 12 may have a slot 40 that extends from the proximal end 18 to the distal end 20 to allow flexing of the tip 12. In the illustrated embodiment, the slot 40 extends from the flanged portion 34 to the body portion 30. In an embodiment, the slot 40 may open on the distal end 20 of the gripping tip 12. In accordance with embodiments of the present invention, the slot 40 should generally allow flexing of the gripping tip 12 so that the first and second jaw portions 22, 24 can clamp down on an implant 72 or release the implant. For example, the first and second jaw portions 22, 24 may clamp down into the lateral slots 134 of the implant 72. As illustrated, the slot 40 may narrow in the beveled portion 33 of the body portion 32.

Figure 26:
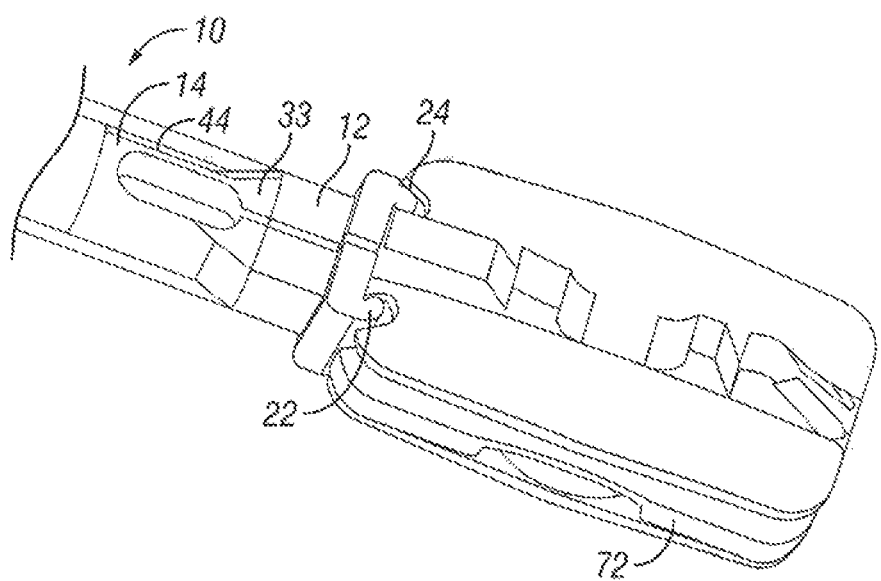
FIG. 26 is a perspective view a gripping tip of an insertion tool assembly in a locked position and holding an implant in accordance with one embodiment of the present invention.

FIG. 26 illustrates the insertion tool assembly 10 of FIG. 25 with the gripping tip 12 in a locked position and holding the implant 72 in accordance with one embodiment of the present invention. The insertion tool assembly 10 may be placed in the locked position, for example, to secure the gripping tip 12 to the implant 72. The implant 72 may be positioned, for example, with the protrusions 140 positioned in the corresponding openings 138 in the implant 72. The outer sleeve 44 of the sleeve assembly 14 may then be forced down and onto the gripping tip 12. As the outer sleeve 44 engages the beveled surface 33 of the gripping tip 12, the gripping tip 12 should flex, clamping the first and second jaw portions 22, 24 into the corresponding lateral slots 134 of the implant 72. In this manner, the implant 72 may be rigidly fixed to the insertion tool assembly 10 in accordance with one embodiment of the present invention. The surgeon may then maneuver the implant 72 to the desired position in the patient, for example. Once the implant has been maneuvered to the desired position within the patient, the implant may be released from the gripping tip. Any of a variety of different techniques may be utilized to cause the insertion tool assembly 10 to release the implant 72 when desired. For example, a plunger 51 (see, e.g., FIG. 6) may be inserted into the slot 40 to force apart the first and second jaw portions 22, 24.

FIGS. 27-30 illustrate a gripping tip 12 that may be used to secure an implant 72 to an insertion tool assembly 10 in accordance with one embodiment of the present invention. As illustrated, the gripping tip 12 includes body portion 32, flanged portion 34, and arms 142. The flanged portion 30 may be disposed on the distal end 20 of the gripping tip 12. In the illustrated embodiment, the gripping tip 12 has one or more (e.g., two) arms 142 coupled to the body portion 32. As illustrated, the gripping tip 12 may include two arms 142 on opposing sides of the body portion 32. The arms 142 may be movably coupled to the body portion 32. Each of the arms 142 may include a jawed end 144. The arms 42 may be configured to swing closed forcing the jawed ends 144 to clamp onto the implant 72 securing the implant 72 to the insertion tool assembly 10. In an embodiment, the jawed ends 144 may be configured to engage with the lateral slots 134 in the endplates 74 of the implant 72. As illustrated, the jawed ends 144 may be generally curved or rounded in shape. One or more (e.g., two) projections 140 may extend outwardly and longitudinally from the flanged portion 34. The projections 140 may be, for example, round or elliptical pins. The projections 140 may be generally configured to engage with corresponding openings 138 in the implant 72. In an embodiment, the projections 140 should engage the implant 72 to, for example, stabilize the implant 72 from twisting or being able to articulate.

Figure 27:
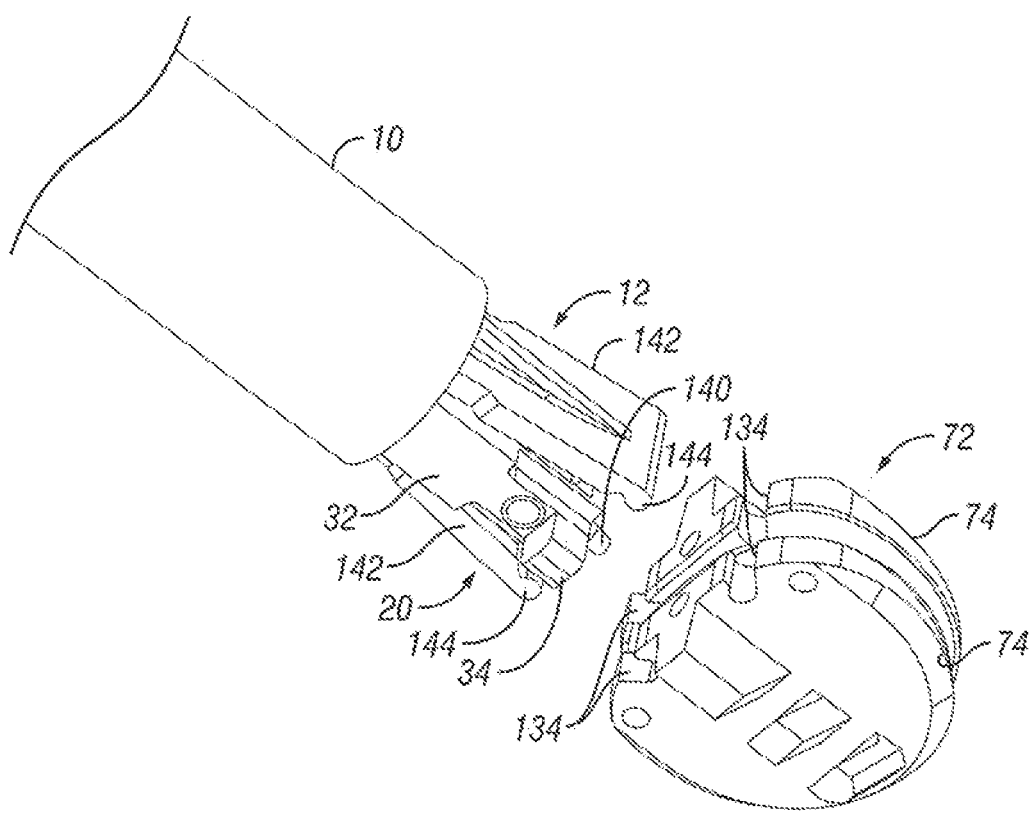
FIG. 27 is a perspective view a gripping tip of an insertion tool assembly and an implant in accordance with one embodiment of the present invention.
Figure 28:
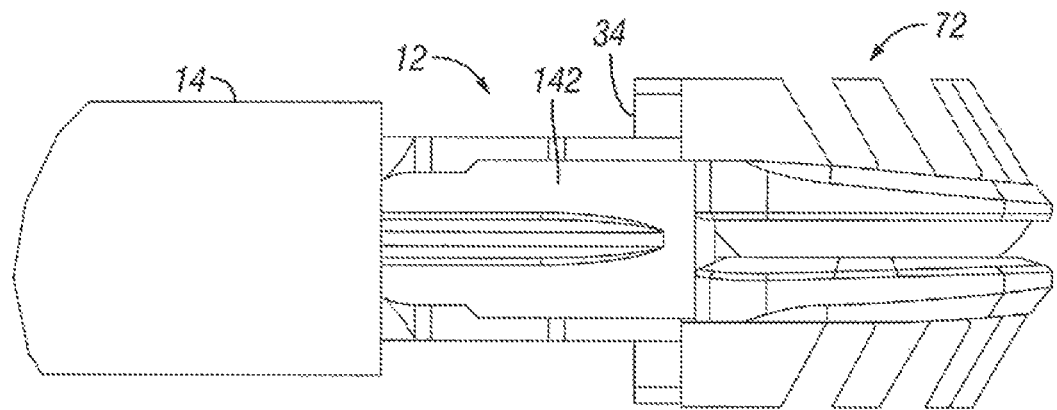
FIG. 28 is a side view of a gripping tip of an insertion tool assembly in a locked position and holding an implant in accordance with one embodiment of the present invention.
Figure 29:
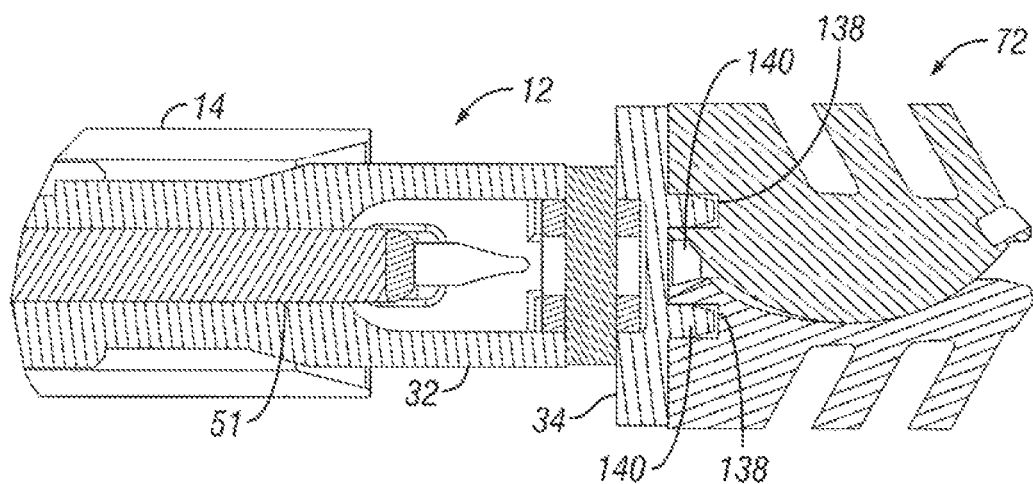
FIG. 29 is a side, cross sectional view of a gripping tip of an insertion tool assembly in a locked position and holding an implant in accordance with one embodiment of the present invention.

FIGS. 28-30 illustrate the insertion tool assembly 10 with the gripping tip 12 of FIG. 27 in a locked position and holding the implant 72 in accordance with one embodiment of the present invention. The insertion tool assembly 10 may be placed in the locked position, for example, to secure the gripping tip 12 to the implant 72. The implant 72 may be positioned, for example, with the protrusions 140 positioned in the corresponding openings 138 in the implant 72. The arms 142 may then be actuated to swing closed. By way of example, a plunger 51 from the sleeve assembly 14 may be pushed into the body portion 32 to force the arms 142 to swing closed. As the arms 142 swing closed, the jawed ends 144 of the arms 142 should to clamp down on the implant 72 in the lateral slots 134. In this manner, the implant 72 may be rigidly fixed to the insertion tool assembly 10 in accordance with one embodiment of the present invention. The surgeon may then maneuver the implant 72 to the desired position in the patient, for example. Once the implant has been maneuvered to the desired position within the patient, the implant may be released from the gripping tip. Any of a variety of different techniques may be utilized to cause the insertion tool assembly 10 to release the implant 72 when desired. For example, the plunger 51 may be removed from the body portion 32 to release the arms 142 causing them to swing open.

While it is apparent that the invention disclosed herein is well calculated to fulfill the objects stated above, it will be appreciated that numerous modifications and embodiments may be devised by those skilled in the art. While devices and methods are described in terms of "comprising," "containing," "having," or "including" various elements or steps, the devices and methods can also "consist essentially of" or "consist of" the various elements and steps.

What is claimed is:

1. An insertion tool assembly for delivering an implant to a surgical site in between adjacent vertebral bodies, the insertion tool assembly comprising:
   a gripping tip having a proximal portion, a body portion, and a distal portion,
   wherein the distal portion comprises a first jaw portion and a second jaw portion, wherein the body portion is disposed between the first and second jaw portions; and
   wherein the gripping tip includes a first drill guide angled upwardly and a second drill guide angled downwardly, wherein the first drill guide is configured to be angled toward a superior vertebral body when the implant is inserted between the adjacent vertebral bodies and the second drill guide is configured to be angled toward an inferior vertebral body when the implant is inserted between the adjacent vertebral bodies.

2. The tool assembly of claim 1, wherein the first drill guide and the second drill guide extend through the distal portion of the gripping tip.

3. The tool assembly of claim 1, wherein the first drill guide comprises a first channel and the second drill guide comprises a second channel, wherein the first channel and the second channel are angled inwardly toward each other.

4. The tool assembly of claim 1, wherein the gripping tip further comprises a slot that extends through the gripping tip to accommodate flexing of the gripping tip.

5. The tool assembly of claim 4, wherein the slot extends through the proximal portion, the body portion and the distal portion of the gripping tip.

6. The tool assembly of claim 1, wherein the first and second jaw portions are configured to flex inwardly toward one another when in a locked position.

7. The tool assembly of claim 1, wherein the gripping tip further comprises a first inwardly extending portion that is distal to a first recess and a second inwardly extending portion that is distal to a second recess.

8. The tool assembly of claim 1, wherein the gripping tip comprises a flanged portion.

9. The tool assembly of claim 8, wherein the flanged portion includes the first drill guide in the form of a first channel and the second drill guide in the form of a second channel.

10. The tool assembly of claim 1, wherein the gripping tip further includes a keyed protrusion configured to engage a corresponding recess on an implant.

11. The tool assembly of claim 1, wherein the gripping tip is configured to engage an implant and fixedly couple the implant to the insertion tool assembly.

12. An insertion tool assembly for delivering an implant to a surgical site in between adjacent vertebral bodies, the insertion tool assembly comprises:
   a handle assembly;
   a sleeve assembly extending from the handle assembly; and
   a gripping tip operably connected to the sleeve assembly, wherein the gripping tip comprises a proximal portion, a body portion and a distal portion, wherein the distal portion comprises a first jaw portion and a second jaw portion, wherein the body portion is disposed between the first and second jaw portions,
   wherein the gripping tip includes a first drill guide angled upwardly and a second drill guide angled downwardly, wherein the first drill guide is configured to be angled toward a superior vertebral body when the implant is inserted between the adjacent vertebral bodies and the second drill guide is configured to be angled toward an inferior vertebral body when the implant is inserted between the adjacent vertebral bodies.

13. The tool assembly of claim 12, wherein the first drill guide and the second drill guide extend through the distal portion of the gripping tip.

14. The tool assembly of claim 12, wherein the first drill guide comprises a first channel and the second drill guide comprises a second channel, wherein the first channel and the second channel are angled inwardly toward each other.

15. The tool assembly of claim 12, wherein the gripping tip further comprises a slot that extends through the gripping tip to accommodate flexing of the gripping tip.

16. The tool assembly of claim 15, wherein the slot extends through the proximal portion, the body portion and the distal portion of the gripping tip.

17. The tool assembly of claim 12, wherein the first and second jaw portions are configured to flex inwardly toward one another when in a locked position.

18. The tool assembly of claim 12, wherein the gripping tip further comprises a first inwardly extending portion that is distal to a first recess and a second inwardly extending portion that is distal to a second recess.

19. The tool assembly of claim 12, wherein the gripping tip comprises a flanged portion.

20. The tool assembly of claim 19, wherein the flanged portion includes the first drill guide in the form of a first channel and the second drill guide in the form of a second channel.

* * * * *